United States Patent [19]

Wellisz

[11] Patent Number: 5,752,958
[45] Date of Patent: May 19, 1998

[54] BONE FIXATION PLATE

[76] Inventor: Tadeusz Z. Wellisz, 536 S. Rimpau Blvd., Los Angeles, Calif. 90020-4832

[21] Appl. No.: 831,906

[22] Filed: Apr. 2, 1997

[51] Int. Cl.$^6$ ........................................... A61B 17/80
[52] U.S. Cl. ........................................ 606/69; 606/72
[58] Field of Search ........................ 606/69, 70, 71, 606/72, 73, 61, 60

[56] References Cited

U.S. PATENT DOCUMENTS

| | | |
|---|---|---|
| 4,587,963 | 5/1986 | Leibinger et al. . |
| 4,763,548 | 8/1988 | Leibinger et al. . |
| 5,201,737 | 4/1993 | Leibinger et al. . |
| 5,263,980 | 11/1993 | Leibinger et al. . |
| 5,372,598 | 12/1994 | Luhr et al. ............................ 606/69 |
| 5,413,577 | 5/1995 | Pollock ................................. 606/69 |
| 5,468,242 | 11/1995 | Reisberg .............................. 606/69 |
| 5,578,036 | 11/1996 | Stone et al. ......................... 606/69 |

FOREIGN PATENT DOCUMENTS

| | | |
|---|---|---|
| 433852 | 12/1990 | European Pat. Off. . |
| 4028021 | 5/1991 | Germany . |

*Primary Examiner*—Guy V. Tucker
*Attorney, Agent, or Firm*—William W. Haefliger

[57] ABSTRACT

A surgical connector that comprises a grid plate having multiple holes therethrough, and distributed over the plate area; there being plate material in the form of a ring extending about each hole; the plate defining multiple ribs; three of the ribs connecting each ring with three others of the rings.

14 Claims, 3 Drawing Sheets

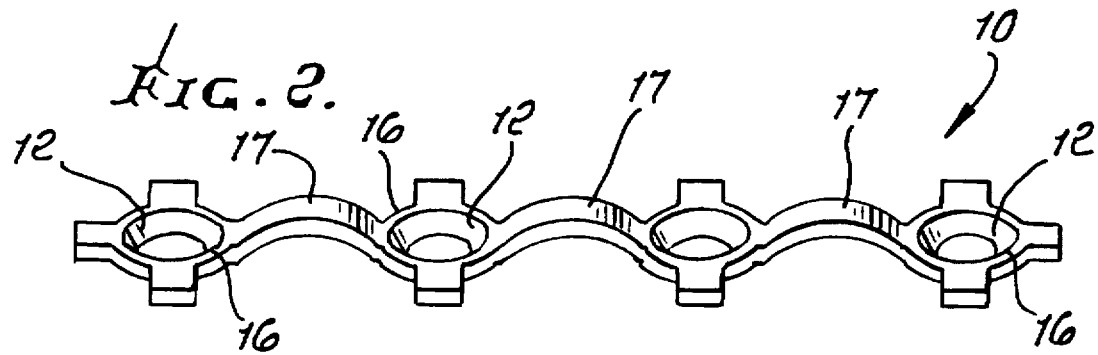
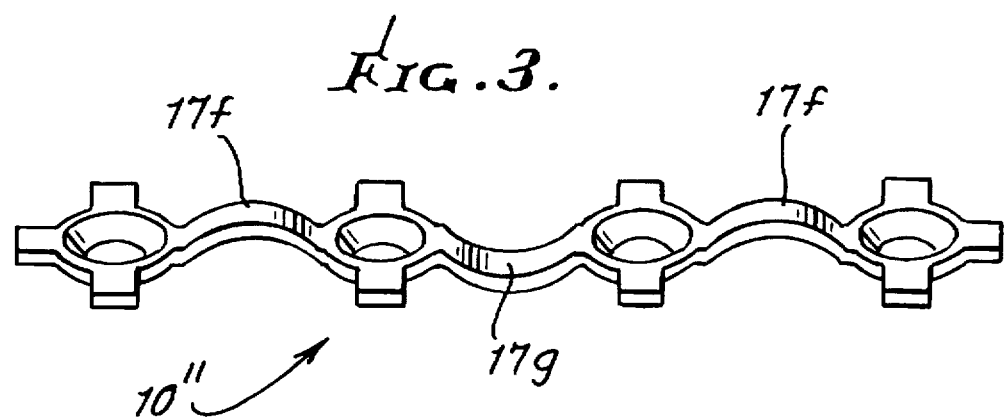
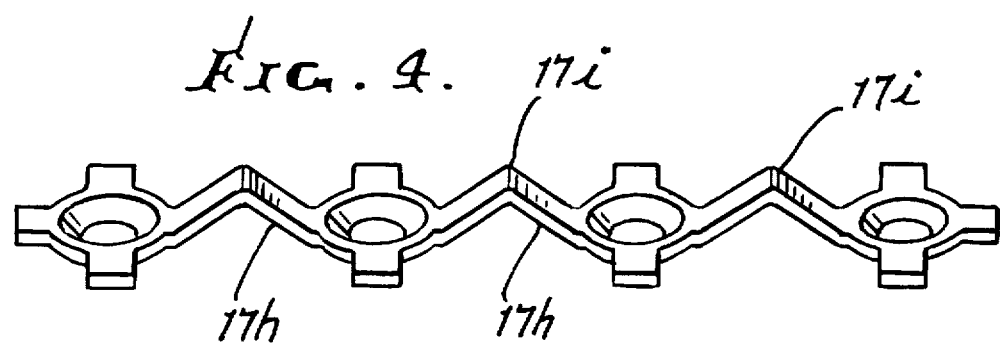
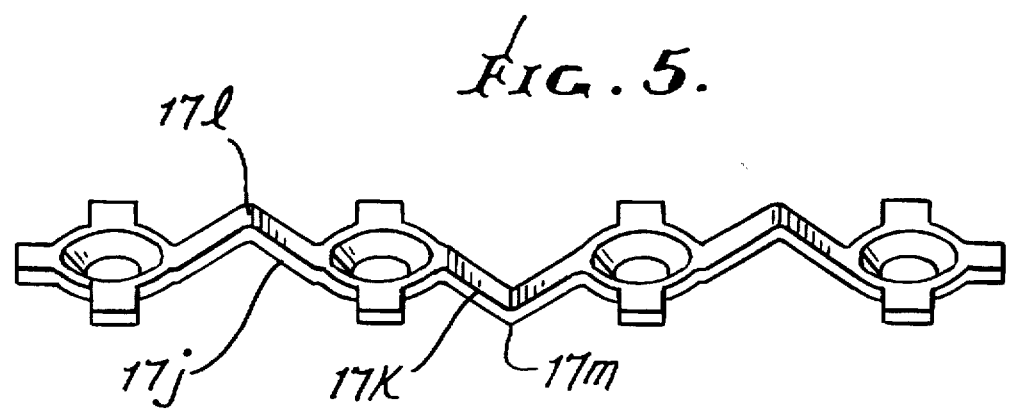

BONE FIXATION PLATE

BACKGROUND OF THE INVENTION

This invention relates generally to fixation plates used for fixation of bone tissue, for example to stabilize fractures, and more particularly, to improvement in such plates having grid configuration facilitating use of such plates.

Bone fixation plates and fasteners are used to align and stabilize fractures of bony tissue, while normal tissue healing occurs. Bone plate and fastener fixation systems are intended for use in the treatment of fractures, osteotomy procedures, and reconstructive procedures. Fixation systems include a variety of plate configurations for different anatomical applications. Screws or other fasteners are included for fixation of the plates to the bony tissue.

Traditional bone plates are linear constructs that contain holes to accept fasteners that attach the plate to the underlying bone. Many plates are designed to be malleable to allow them to be contoured by the end user to adapt to the contour of the bone.

Sheets, grids, screens, and mesh plates can also be used to stabilize bony tissue. They can also span gaps in bony tissue and can serve to provide structural support, restore the contour of the tissue and act as a barrier between tissue planes. They can be contoured by bending, folding, or rolling. Rolling can be useful when a mesh plate is to be adapted to a tubular structure, such as a long bone.

The ability to adapt sheets, grids, screens, and mesh plates to complex three-dimensional shapes, such as those present in the craniofacial skeleton, is limited. This is because, although sheets, grids, screens, and mesh plates are malleable, they are not designed to stretch, and the distances between the holes for the fasteners, as measured along their surface, remain essentially unchanged as bending, folding, or rolling takes place. An analogy is the ability to wrap a piece of paper around a spherical object, such as a ball: doing so will result in pleats and folds in the paper. If such a pleat or fold were to occur in a sheet, grid, screen, or mesh plate used to stabilize bony tissue, both a weakening of the fixation and a contour deformity could occur.

There is great need for fixation plates configured to overcome problems and difficulties in their use, for example as referred to above.

SUMMARY OF THE INVENTION

It is a major object of the invention to provide an improved device used to stabilize, fixate or align bony or cartilagenous tissue. As will be seen, the device is made of a malleable, implantable material, such as a biocompatible metal or polymer. The device, partially or in its entirety, has the shape of a lattice with curved members, such as arms or ribs, that intersect in such manner as to accommodate provision of holes that accept fasteners. Such holes may be located at the points of intersection of the arms, or elsewhere. The distances between the points of intersection of some or all of the arms, can be varied to allow the device to be shaped to fit a precise three-dimensional contour, or the contour of bony or cartilageous tissue.

The device can be used with fasteners allowing for the distance between the fasteners to be varied for precise matching to three-dimensional alignment of the bony tissue. The fact that the arms connecting the holes in the mesh are curved allows the distances between the individual holes to be changed, thus allowing for contouring in three dimensions.

Accordingly, it is a further object to provide a device as referred to, and characterized by, provision of:

a) a grid plate having multiple holes therethrough, and distributed over the plate area, b) there being plate material in the form of a ring extending about each hole, c) the plate defining multiple ribs, d) three of the ribs connecting each ring with three others of the rings.

As will appear, the ribs are preferably curved, to allow for differential expansion of the device to fit three-dimensional contours, as for example dished eye orbits in the skull. In this regard, the holes may be advantageously arranged and spaced apart in hexagonal clusters.

Another object is to provide such a device wherein the rings about the holes in each cluster include three pairs of rings, the rings of each pair interconnected by a curved rib. In this regard, the pair of holes associated with each pair of rings are preferably included in two adjacent hexagonal clusters of holes.

Yet another object is to provide a connector grid plate easily deformed to have compound curvature, to fit more precisely to bony structure having corresponding compound curvature.

An additional object is to provide an improved grid plate having multiple spaced and curved ribs that project out of the plane of the plate, with smooth curvature or with angled configuration.

These and other objects and advantages of the invention, as well as the details of an illustrative embodiment, will be more fully understood from the following specification and drawings, in which:

DRAWING DESCRIPTION

FIG. 2 is an edge view of the FIG. 1 connector;

FIG. 3 is a view like FIG. 2 showing a modification;

FIG. 4 is another view like FIG. 2 showing another modification;

FIG. 5 is yet another view like FIG. 2 showing a further modification;

DETAILED DESCRIPTION

Figure 1:
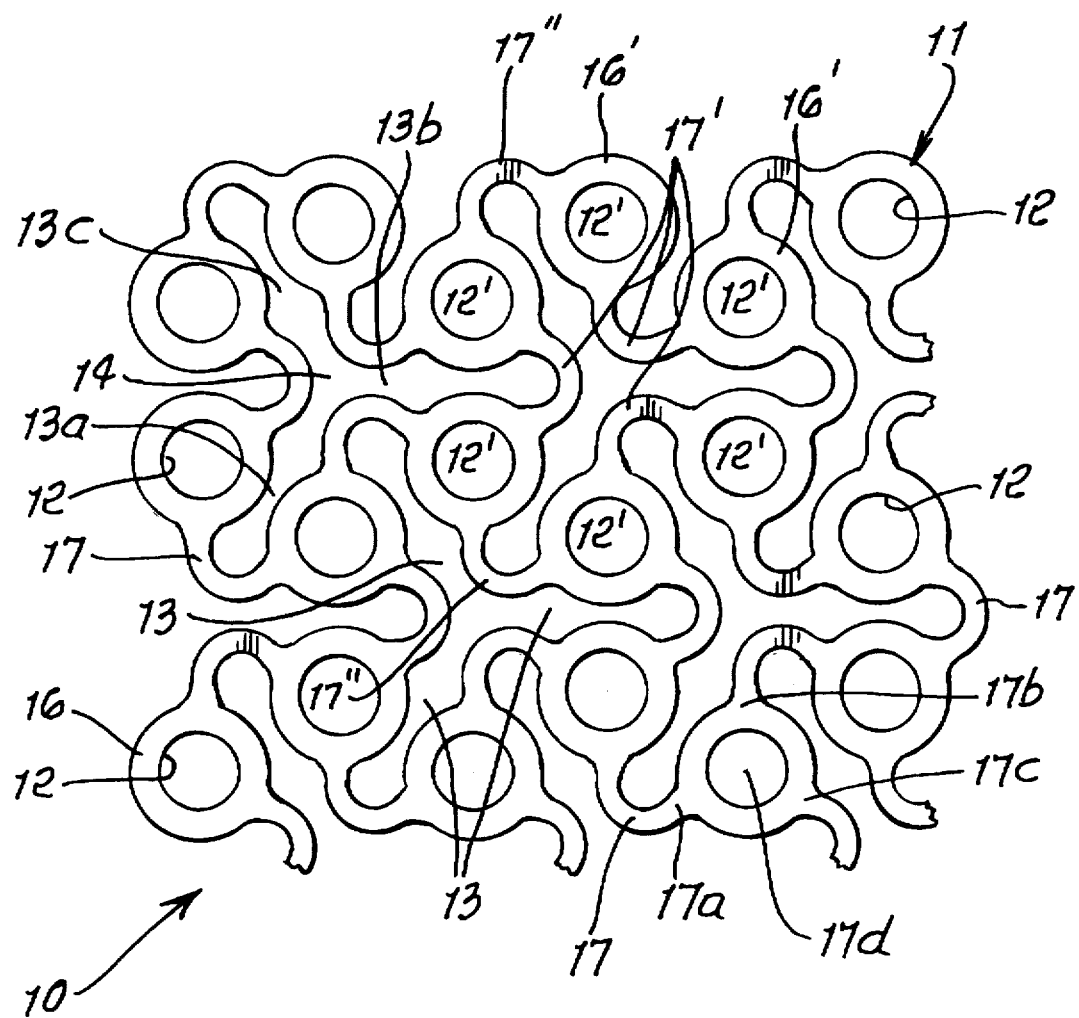
FIG. 1 is an enlarged plan view of the surgical connector of the invention.

Referring first to FIG. 1, a surgical connector 10 (which may be considered as preferred) includes a grid plate 11 having multiple like circular holes 12 extending through the plate structure, and also distributed over the plate area, as shown. There are also like, three-legged, elongated openings 13 extending through the plate structure, as defined for example by legs 13a, 13b, and 13c projecting radially from a center 14 extending through the plate, and with equal angles, such as 120° angles formed between such legs.

Plate material in the form of a ring 16 extends about each hole 12, and the plate also defines multiple, like connector ribs or arms 17. As shown, three of the ribs connect each ring with three others of the rings. Note that the connector points 17a, 17b, and 17c of the ribs with each ring are distributed at equal angles, i.e., 120° with respect to the ring center 17d, which is also the hole center, each ring being generally circular.

It will further be noted that the holes 12 are arranged or distributed in hexagonal clusters; that the rings about the holes in each cluster include three pairs of rings; and the rings of each pair are interconnected by a curved rib. See for example the hexagon cluster defined by holes 12', and the curved ribs 17' and 17" connecting the rings 16' extending about the holes 12'. Alternate of the ribs, as for example three ribs 17', project toward the center of the cluster; and the remaining three ribs 17" project away from the center of the cluster. Further, the pair of holes associated with each pair of rings is included in two adjacent like hexagonal clusters of holes.

As shown in FIGS. 1 and 2, the grid plate 11 defines a plane (for example the plane of FIG. 1, and certain of the ribs 17 (for example all such ribs) project upwardly from the plane; as shown in FIG. 2, the ribs 17 project upwardly with convexity. Therefore, the ribs 17 have compound curvature, i.e., as seen in FIG. 1 and as seen in FIG. 2.

Figure 6:
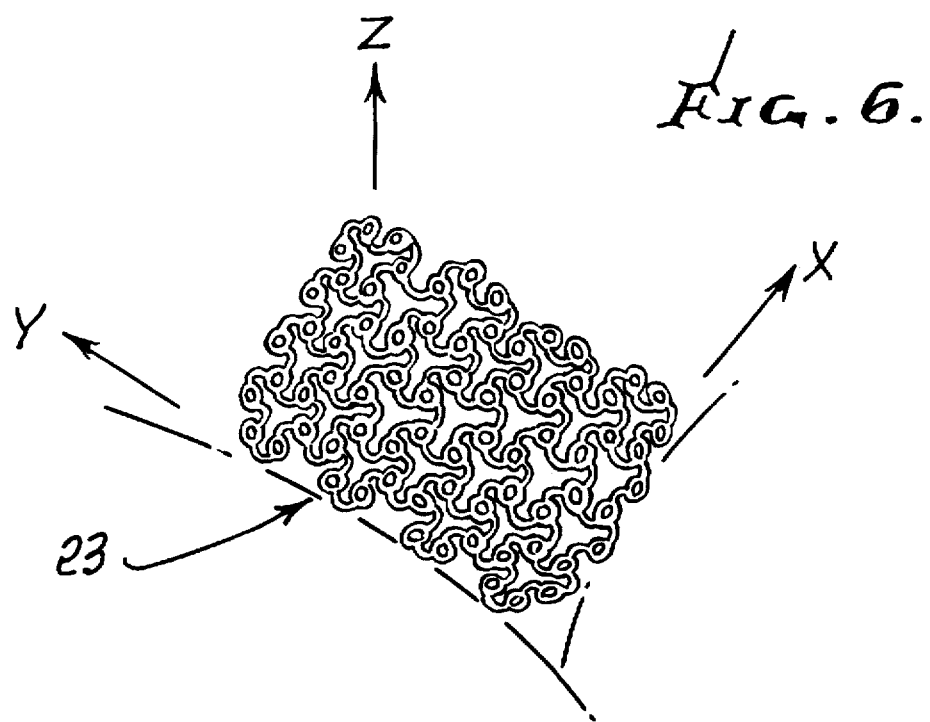
FIG. 6 is a perspective view of the FIGS. 1 and 2 connector, deformed to have compound curvature.
Figure 7:
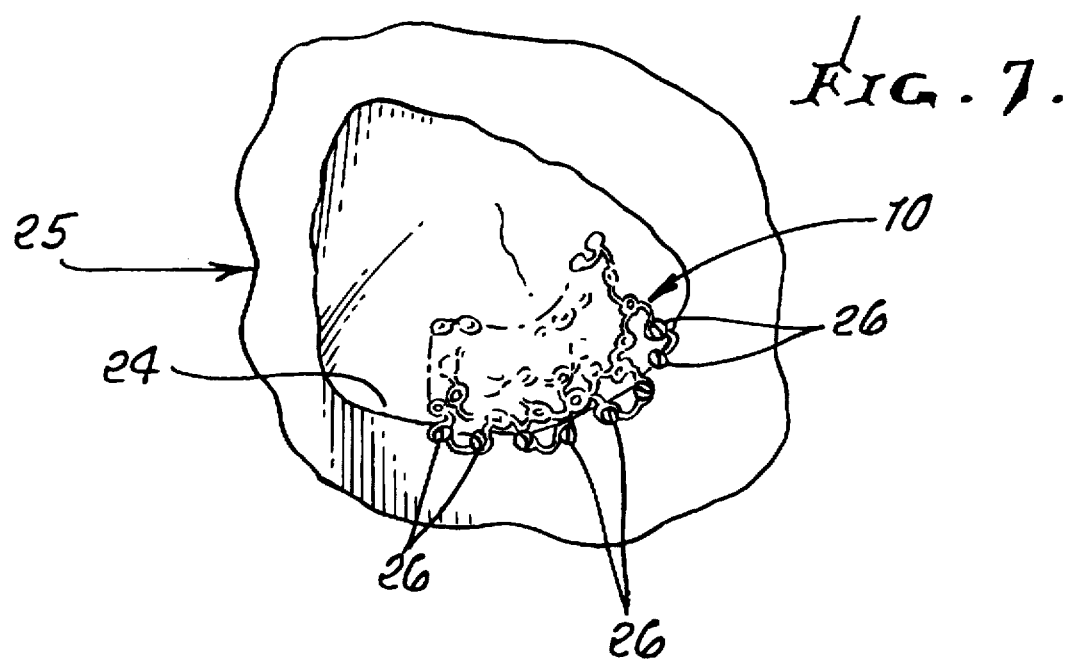
FIG. 7 is a view showing use of the connector deformed as in FIG. 6.

The configuration as shown and described is found to have a high degree of manual deformability to provide selectable plate compound curvature, as for example is illustrated at 23 in FIG. 6 wherein the plate has dome shape. It is curved convexly upwardly in X-Z planes, and also in Y-Z planes of an X-Y-Z rectangular coordinate system, as illustrated. This shaping of the plate allows it to be easily and advantageously closely fitted to bone structure surfaces having compound curvature. See for example the orbital lower wall 24 of a human skull 25 shown in FIG. 7, to which the plate 10 is fitted by manual deformation, including local stretching. Fastener means 26 at the edge of the orbital wall attach the plate to the skull. Wall extends directly below the human eye.

FIG. 3 shows alternate ribs 17f and 17g of a multiple plate 10", projecting convexly upwardly and downwardly, relative to the plane of the plate.

FIG. 4 shows modified ribs 17h projecting angularly upwardly, to form peaks 17i; and FIG. 5 shows alternate modified ribs 17j and 17k projecting angularly upwardly and downwardly to form peaks 17l and 17m.

A preferred plate, as described, consists of titanium, although stainless steel and synthetic polymers (such as polyethylene or polypropylene) are usable. Poly-lactic and poly-gelactic materials are also usable.

Between 0.2 and 0.5 of the plate overall area is solid material, allowing plate stretachability or expansion in three directions (X, Y, and Z directions in a rectangular coordinate system). Center-to-center distance between holes 12 connected by a rib is between 0.180 and 0.14 inches; hole 12 diameters are between 0.067 and 0.035 inches; outer diameter of the rings 16 are between 0.125 and 0.160 inches; and the radii of the circularly curved ribs 17 are between 0.08 and 0.04 inches. Plate thickness is between 0.012 and 0.025 inches and is generally uniform.

The plate material may be biamenar, or multiamenar; or the plate material may be a composite, such as titanium base, onto which is deposited a polymer or protein layer. The second or outer layer may act as a lattice to promote tissue ingrowth and thus healing. An example is a second or outer layer consisting of polyethylene granules. In this regard, healing of bone is frequently delayed or incomplete. It is known that certain substances, generally referred to as growth factors, can increase the rate and/or the amount of bone healing. One issue pertaining to the use of growth factors is that they are rapidly cleared from the body by the body's circulatory system. The ability to bind the growth factors to a polymer or protein layer may have the effect of localizing and prolonging the activity of the growth factors. The defect would require structural support until such time that the defect was to heal.

I claim:

1. A surgical connector comprising:

a) a grid plate having multiple holes therethrough, and distributed over the plate area, b) there being plate material in the form of a ring extending about each hole, c) the plate defining multiple arcuate ribs, d) three and only three of said ribs connecting each ring with three others of said rings, respectively, wherein at least two adjacent rings define a plane and are connected by an arcuate rib projecting upwardly of said plane.

2. The connector of claim 1 wherein said holes are arranged in hexagonal clusters.

3. The connector of claim 2 wherein the rings about the holes in each cluster include three pairs of rings, the rings of each pair interconnected by a acruate rib.

4. The connector of claim 3 wherein the pair of holes associated with each pair of rings are included in two adjacent hexagonal clusters of holes.

5. The connector of claim 1 wherein the plate is deformable to have compound curvature defining a dome.

6. The connector of claim 5 including bone structure having surface compound curvature generally matching that of said plate, there being by fasteners passing through said holes, said fasteners adapted to retain the plate dome nested to bone structure compound curvature.

7. The connector of claim 1 wherein the plate is deformable in an X, Y, Z rectangular coordinate system, the plate having curvature in X-Z planes, and the plate having curvature in Y-Z planes.

8. The connector of claim 1 wherein the plate defines a plane, certain of said ribs projecting upwardly from said plane.

9. The connector of claim 8 wherein said certain ribs have one of the following:

i) upward convexity ii) upward angularity defining crests.

10. The connector of claim 1 wherein the plate defines a plane, certain of said ribs projecting generally downwardly from said plane.

11. The connector of claim 9 wherein said certain ribs have one of the following:

i) upward convexity ii) upward angularity defining peaks.

12. The connector of claim 1 including fasteners passing through said holes.

13. The connector of claim 1 wherein there are also like clusters of three-legged openings through said plate, said three-legged openings bounded by said rings or ribs.

14. The connector of claim 1 wherein the plate is characterized by at least one of the following:

i) center-to-center distances between holes connected by a rib is between 0.180 and 0.14 inches, ii) hole diameters are between 0.062 and 0.035 inches, iii) outer diameters of the rings are between 0.125 and 0.160 inches, iv) the ribs are circularly curved and have radii between 0.08 and 0.04 inches.

* * * * *